United States Patent [19]

Hassler

[11] 4,275,595

[45] Jun. 30, 1981

[54] PROCESS AND INSTALLATION FOR PRODUCING AND RECORDING ULTRASONIC SECTIONAL IMAGES

[75] Inventor: Dieter Hassler, Erlangen, Fed. Rep. of Germany

[73] Assignee: Siemens Aktiengesellschaft, Berlin & Munich, Fed. Rep. of Germany

[21] Appl. No.: 5,864

[22] Filed: Jan. 23, 1979

[30] Foreign Application Priority Data

Feb. 14, 1978 [DE] Fed. Rep. of Germany ....... 2806176

[51] Int. Cl.$^3$ ........................ G01N 29/00; H04N 3/00
[52] U.S. Cl. ........................................ 73/606; 358/112
[58] Field of Search .................. 73/606, 607, 618, 620, 73/625, 626; 128/660; 367/7, 11; 358/112, 166

[56] References Cited

U.S. PATENT DOCUMENTS

| 4,135,140 | 1/1979 | Buchner | 73/626 |
| 4,167,753 | 9/1979 | Lynk | 358/112 |
| 4,174,705 | 11/1979 | Buchner | 367/7 |

FOREIGN PATENT DOCUMENTS

2501559 7/1977 Fed. Rep. of Germany .

*Primary Examiner*—Stephen A. Kreitman
*Attorney, Agent, or Firm*—Hill, Van Santen, Steadman, Chiara & Simpson

[57] ABSTRACT

In an exemplary embodiment, an examination object is scanned line-by-line with an ultrasonic beam and the developing echo signals are correspondingly recorded line-by-line on an image recording installation to form a visible image. The echo recording is to ensue amplitude-compressed without a simultaneous deterioration of the resolution or of the image sharpness. To this end, a preselectable plurality of echo lines ($Z_n$ through $Z_{n+3}$) which preferably determine the breadth of a surround field for echoes to be depicted together with a current line ($Z_{n+4}$) are always written into intermediate memories. Subsequently, the stored and, under certain conditions, current echo signal information are supplied to an evaluation installation. During a specific section time, which determines the depth ($\tau$) of the surround field, a mean value of the echo intensity in the surround field is here at least approximately comprehended. This, if necessary after previous dynamic limitation, is placed in ratio at a ratio former to the echo respectively to be depicted. The ratio signal is the recording signal for the recording installation.

22 Claims, 5 Drawing Figures

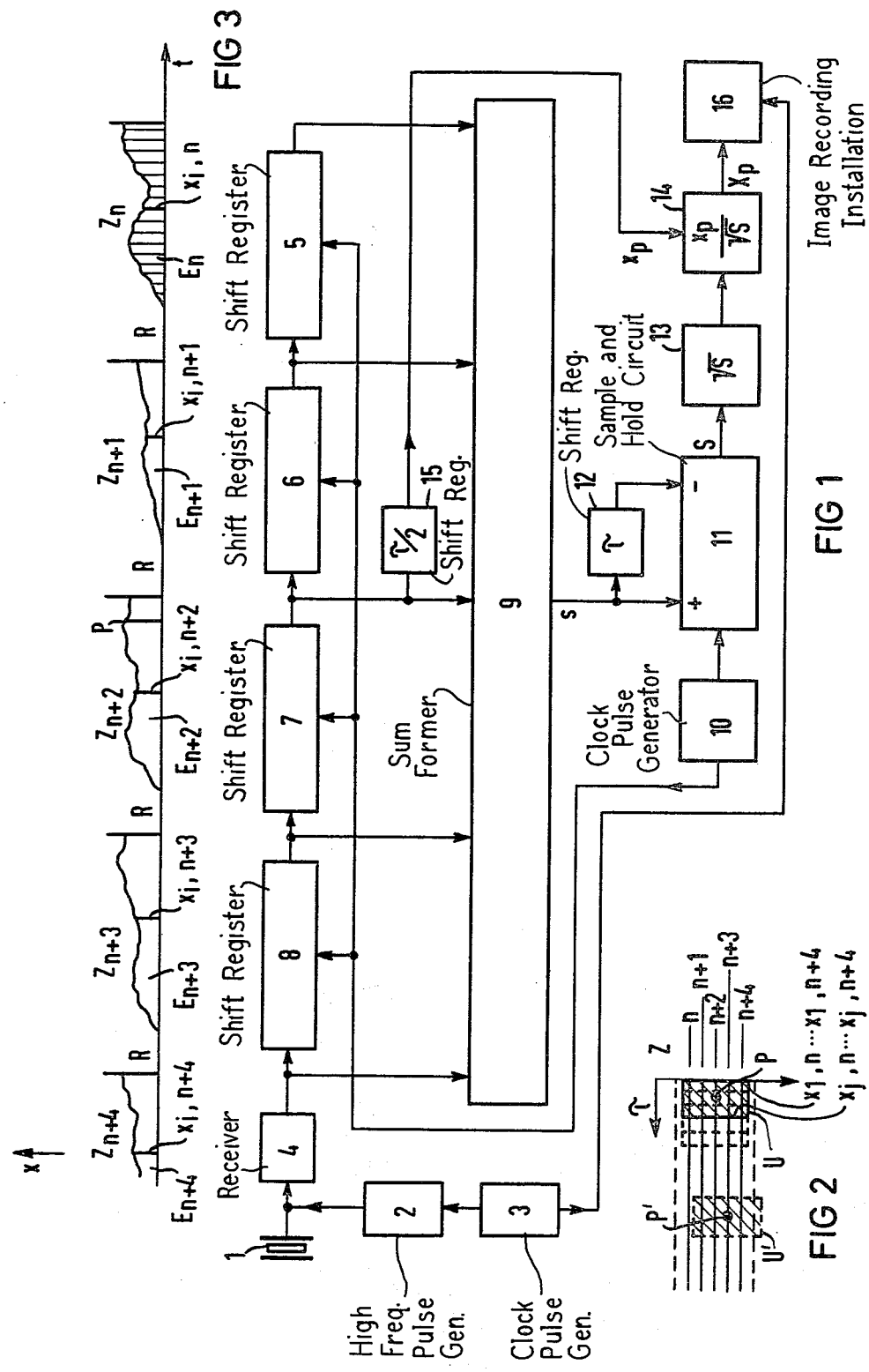

PROCESS AND INSTALLATION FOR PRODUCING AND RECORDING ULTRASONIC SECTIONAL IMAGES

BACKGROUND OF THE INVENTION

The invention relates to a process and to an installation for producing and recording ultrasonic sectional images, whereby an examination object is scanned line-by-line with ultrasonic transmission signals and the developing echo signals are correspondingly recorded on the recording medium of an image recording installation to form a visible image. By recording medium of an image recording installation, the screen of an oscillograph tube is particularly to be understood. However, in the broadest sense, the recording media of recorders of any type are also included which, on the basis of line-, point-, droplet recording or etc., produce visible images on the medium, which are modulated in their optical density structure or color structure, too, as a function of the intensity of developing echo signals.

In known sectional image recording devices, the effect arises that in medium image areas and image areas near the skin, the dynamic range of the electric echo signals is significantly higher than that amplitude range which can be reproduced with intensity modulation of the recording beam in the visible image of the recording installation. Thereby, however, significant information is lost which could contribute to a better image interpretation. If, for instance, the image recording ensues with low amplification, then specific structures in the median image area and in the image area near the skin can be depicted well in outline but already less well in the inner fine structures. One obtains the latter information when the amplification is increased. Thereby, however, image areas that are already well structured are swamped and thus lose their richness of detail or their resolution. In view of this disadvantage, an image reproduction is desirable which unites in a single image those diagnostically valuable image parts of the recording image obtainable with low amplification and those obtainable with higher amplification.

Such a unification to a total image could indeed be attained with a photographic trick by means of so-called dodging (and/or burning-in) technology, where, upon producing a positive image in the photolab, those places of an ideal negative in which an overexposure is to be feared are covered (are dodged) for a certain time. Thus, details are retained which would otherwise be submerged in the black image passages. This technique, however, is rather expensive in comparison to the degree of image improvement attained. Moreover, in a visible image obtained with low amplification it must be expected that the contour will break up because the echoes of structures which are not struck perpendicularly decrease, as a function of the angle, very quickly the more tangential the sonic beam strikes. The practitioner therefore generally uses a different process, which is based on the fact that he changes the amplification during the examination at varying applicator positions and photographs the visible image which is respectively produced. The subsequent comparison of the various photos then allows the diagnostic statement. As long as attention is being directed toward a limited image area, this procedure is certainly acceptable since it is not connected with costs that are all too high. If, however, an ultrasonic sectional image is to be evaluated in its totality, then disadvantages that are not insignificant result. The human brain as a memory and computer is now placed under significantly higher demands. The demands can indeed be reduced in that the image adjustment is always repeatedly manually changed (wobbled) so that at least the process of remembering is assisted. This procedure, however, is only a crutch which takes time and also, particularly, renders the documentation more difficult.

Further possibilities for improving the visible image ensue in that one either works with color coding in the visible image or with dynamic compression in the echo reception signal. Color coding, however, easily leads to misinterpretations, since each color change in the visible image is automatically interpreted by the human eye in a contour. The dynamic compression indicated could be undertaken by means of non-linear amplitude distortion, for instance logarithmizing at a diode. The problem, however, results that then all interference effects, particularly also the unsharp temporal limitations of the scanning beam including the side lobes are greatly boosted, so that specifically the cross resolution deteriorates.

From the periodical "Fernseh- und Kino-Technik", No. 11/1976, Pages 388 to 392 or, also from "nachrichten elektronik" 1, 1977, Pages 11 and 12, a local-adaptive image processing process for brightness equalization of unevenly illuminated television images is known in the area of television technology. Specifically in this case, the dynamic problem ensues for example in the case of images with strong shadows. Upon an optimum adjustment of the bright part of the picture, details can no longer be seen in the shadow area. That is alleviated by means of dynamic compression which renders a brightening of the shadow area possible. To that end, the integral brightness of the image point to be represented is measured in a surround field by means of a second television picture that is taken unsharp and the brightness of the point is boosted in the inverse ratio to the measuring result. In the case of a very dark surround field, this thus means a strong boost; in the case of a bright surround field a corresponding weaker boost. In this manner, thus, a reduction of the image dynamic range ensues without influencing the detail contrast of the image.

Such a solution applied to the ultrasonic sectional image would, thus, for example, assist the orientation in the search process (for example, pancreas, placenta), because the adjustment of the image parameters (amplification, depth compensation) is less critical. Localization diagnostics would be significantly enriched because of the improved representation of curved organ boundaries. The resolution (image sharpness) would remain unaffected in this type of compression because the amplitude relationship of the desired to the undesired image points (of side lobes) remains unaltered. Thereby, the surround field would have to be selected large enough so that echoes of main and side lobes can be simultaneously comprehended. Then the main lobe echo would ensure that the intensification of the side lobe echoes remains small and that these are not accentuated. Only such structure echoes which lie at a greater lateral interval would be prepared out of the relatively dark surround field by means of amplification boosting. One could then think of transforming the signals of the ultrasonic image in television standard (BAS) and using a television set for representation which functions according to the process of dynamic compression described above. That, however, presupposes that the rectification and data conversion must be executed in a significantly greater dynamic range than is necessary for a simple, uncompromised representation. However, specifically in view of the speed of the processes, this causes problems, so that the transduction would become expensive.

SUMMARY OF THE INVENTION

The object of the present invention is to transform the compression process known from television technology in such manner that, with the smallest possible technical outlay, the compression can be undertaken directly on the electric ultrasonic signal independently of a conversion in television standard.

The object is inventively achieved with a process of the type initially cited in that before transmitting the echo signals to the image recording installation a preselectable plurality of lines which determine, preferably together with a current line, the breadth of a surround field for echoes to be depicted are respectively written in temporal succession in the rhythm of the echo line onset into a correspondingly prescribed number of intermediate memories, which lines are subsequently scanned with a read-out rate which preferably corresponds with the read-in rate; and in that the echo signal information thereby respectively developing is then supplied to an evaluation installation for evaluation to the end that, during a prescribed section scan time which determines the depth of the surround field for echoes to be depicted in the line field, a mean value of the echo intensity in the surround field is at least approximately obtained and, after prior dynamic limitation if necessary, placed in ratio to the echo respectively to be depicted in a ratio former; and in that the ratio signal is the recording signal for the recording installation.

An installation for implementing this process is inventively characterized by a prescribed number (for example, four) of intermediate memories into which a preselectable plurality (likewise four) of lines can be respectively written in temporal succession in the periodicity of the echo line onset; and by a clock generator allocated to the intermediate memories for reading-out the intermediately stored echo information at a prescribed reading-out rate which preferably corresponds to the reading-in rate; as well as by an evaluation installation for the echo signal information at the output of the intermediate memories for the purpose of determining a mean value; and by a ratio former for forming the ratio of an echo signal of the surround field to be depicted and the mean value signal at the output of the evaluation installation which, if necessary, has also been previously dynamically limited.

According to the invention, thus, for echoes respectively to be depicted, a surround field of relatively small extent is formed which co-migrates along the lines during the ultrasonic scanning. For each echo to be depicted, then, a mean value of the intensity of the echoes immediately surrounding this echo can be formed from this surround field. By means of the subsequent ratio formation between the intensity of the echo to be depicted and the intensity of the surround field allocated to this echo, the desired local adaption or dynamic compression then ensues. Thereby, one attains the inventive solution with the technically smallest outlay for memory and other processing means, in contrast to the total image production with a complete second, unsharp echo image which would occasion a significantly aggravating inroad upon the schematics of the scanning image production with a corresponding, significantly increased technical outlay.

In a particular embodiment of the invention, the mean value of the echo intensity in the surround field can be an intensity value comprehended by means of peak detection of the strongest or one of the respectively strongest echoes in the surround field. However, in another advantageous embodiment of the invention, the mean value can also be formed by means of summation of all echo signal information stemming from the surround field. In the latter case, then, in a particularly advantageous manner, the echo signal information from the same depths of each scan line developing at the intermediate memories is to be conducted to a summing installation and to be summed by this again preferably together with appropriate current values and the sum signals are to be subsequently stored in a further memory unit, whereby the memory time specific to this memory unit determines the depth of the surround field for echoes in the line field to be depicted. Any given echo within the surround field can be selected as the echo to be depicted. However, for reasons of symmetry, it is to be recommended that an echo near the middle or, even better, the middle echo be selected. In such a case, then, the side lobe echoes which in general always lie symmetrically to the main echo are also safely covered by the surround field area. Within such a surround field, a linear and uncompressed echo representation then ensues. If, thus, in a preferred manner, the middle echo is selected as the echo to be depicted, then the mean value of the echo intensity in the surround field, if necessary after a preceding dynamic limitation, should be placed in the ratio former in the ratio specifically to a memory echo which is tapped at the intermediate memories after a delay time which corresponds to one of the lines of the surround field stored for half the line count plus half of the storage time of the other memory unit. This stored echo is then exactly the middle echo sought.

Further advantages and details of the invention derive from the following description of exemplary embodiments on the basis of the accompanying sheets of drawings in connection with subclaims; and other objets, features and advantages will be apparent from this detailed disclosure and from the appended claims.

BRIEF DESCRIPTION OF THE DRAWINGS

FIG. 1 shows a first exemplary embodiment in a basic circuit diagram;

FIG. 2 shows format and forward stepping of a rectiform surround field for echo signals to be depicted according to the basic circuit diagram of FIG. 1;

FIG. 3 is a diagram for illustrating echo signal progressions in each of five successive lines, which may determine the breadth of a surround field;

DETAILED DESCRIPTION

Figure 4:
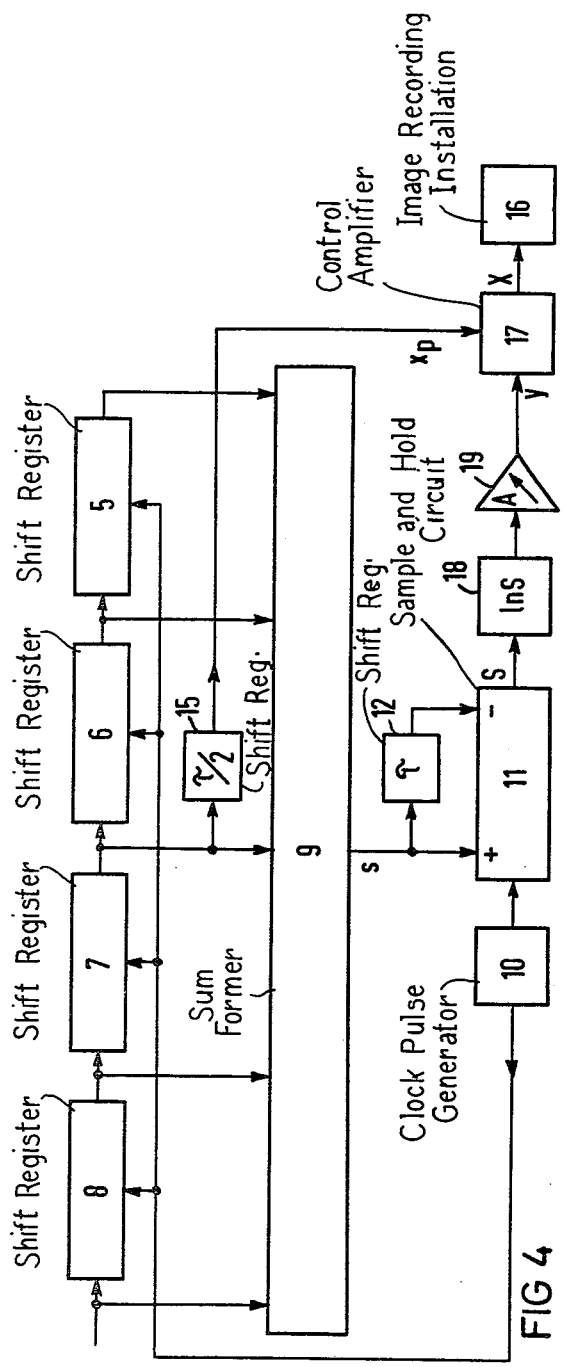
FIG. 4 shows a second embodiment in a basic circuit diagram which is modified in comparison to the embodiment of FIG. 1 with respect to component parts for dynamic compression.

In FIG. 1, 1 designates an ultrasonic transducer which is to scan an examination object, for example, a human body, line-by-line. In the purely schematically illustrated transducer 1, it can be a matter of a so-called rotary transducer with paraboloid reflector; it can, however, also just as well be a matter of a linearly movable transducer or, respectively, of a slueable transducer for effecting, for example, a sector scan. it can also just as well be a matter of a transducer of a compound scan system. In all of these cases, the transducer 1 is fed with high frequency transmission pulses of a high frequency pulse generator 2. The rate of the feed, i.e., the rate of the transmission of ultrasonic pulses by the transducer 1 into an examination object (not illustrated) is predetermined by the clock pulses of a clock pulse generator 3. The echo signals x(t) received from each ultrasonic scanning line in the examination object are supplied in the usual manner to a high frequency reception amplifier 4. In a normal case, the output signals of this amplifier would now be directly supplied as echo pulses for recording on an image recording installation, particularly an electron beam tube.

According to the invention, however, in the present case for each echo to be depicted the appropriate surround field is always formed first and placed in ratio to the intensity of the echo to be depicted. It is then this ratio signal which is supplied to the image recording installation for recording.

In FIG. 2, adapted for the basic circuit diagram of FIG. 1, an image segment with a point P actually to be represented is illustrated in its co-migratory surround field U. Thereby, the surround field respectively comprises five lines $Z_n$ through $Z_{n+4}$, which in their totality determine the breadth of the surround field U. The depth of each surround field is designated with $\tau$. The surround field of each echo pulse to be represented migrates along the lines along with the appropriate echo point. The rate of the forward movement of the surround field is thereby prescribed by means of the reception or, respectively, reproduction rate of echo pulses within a line. In FIG. 3, which shows four respective past lines $Z_n$ through $Z_{n+3}$ together with the current line $Z_{n+4}$, this resolving (or resolution) rate in the line $Z_n$ is indicated with a total of seventeen steps $x_{1, n}$ through $x_{17, n}$. Any given step within the line field is designated with $x_{i, n}$. The other lines are also treated correspondingly, where, in each case, only the $i^{th}$ step $x_{i, n+1}$ for the line $Z_{n+1}$, $x_{i, n+2}$ for the line $Z_{n+2}$, etc., is formally illustrated. Such steps (the first three of a plurality of successive steps) are then also found in the solid line-bordered surround field U for the echo signal P upon its forward stepping with the continuing line. Two further surround fields for further points following the point P (on line $Z_{n+2}$) are indicated by broken lines. A fourth surround field U' for a later echo signal point P' in the line $Z_{n+3}$ is schematically indicated in the left-hand side of FIG. 2.

The subdivision into a total of seventeen steps is meant only as an example. In reality, the point resolution of a line amounts to at least 1 mm. With an image width (corresponding to scanning depth) of 20 cm, for example, this would then effect a resolution of at least two hundred steps per line. In actual realization, then, each surround field thus traverses the line not only in seventeen, but rather in at least a total of two hundred individual steps.

In the exemplary embodiment of FIG. 1, the echo lines respectively developing in temporal succession at the output of the reception amplifier 4 are input into a total of four shift registers 5 through 8 (preferably analog shift registers). With reference to a random surround field U with the lines $Z_n$ through $Z_{n+4}$, this therefore means that the lines $Z_n$ through $Z_{n+3}$ are written into the shift registers 5, 6, 7 and 8 lying in series with one another as past lines in the form illustrated in FIG. 3. The individual values of the line $Z_{n+4}$ are current values which respectively develop immediately. The shift pulse rate for the shift registers 5 through 8 which is adjustable at a clock pulse generator 10 as well as the storage length of the individual registers is selected in such manner that the content of an echo line $E_n$, $E_{n+1}$, etc., together with the appropriate dead time R for the line flyback fits exactly into the respective shift register. In this manner, thus, the echo information from the same depth areas above each line for a total of four lines is found arranged in spatial succession in individual shift registers. By fetching such echo information from the registers by means of the clock pulse generator 10, thus, stored echo values from the same depths for each line always simultaneously develop at the shift register outputs, including (or together with) an appertaining current depth value at the input of the shift register 8. These corresponding depth values of each line are now supplied to a sum former 9 which forms an appropriate sum signal from allocated depth areas of each of the five lines of the concurrent surround field U. The shift pulse rate of the clock pulse generator 10 for the registers 5 through 8 thus effects a quantization of the analog echo signals in the value $x_i$ for varying depth position $i=1$ through j (see FIG. 2), or as a different example $i=0$ through j, within the surround field U. The summing installation 9 adds the respectively homologous $x_i$ of all five lines of the surround field strip. Thus, sum signals result according to the relationship $$s = \sum_{n}^{n+4} x_{i,n}$$

(n=line number).

The summing over successive values of i, however, ensues by means of sample-and-hold circuit 11 in conjunction with a shift register 12 with a storage time $\tau$. The sample-and-hold circuit 11 adds all sum signals of the summing unit 9 in the shift pulse of the clock pulse generator 10. However, via the shift register 12, the sum value of the summing circuit 9 which had already developed before the delay time of the shift register is always respectively subtracted from the stored total sum of the sum signals. In this manner, the surround field migrating in the x-clock rate with the depth extent $\tau$ results according to the relationship $$S = \sum_{i=0}^{i=j} \sum_{n}^{n+4} x_{i,n}$$

This sum value S is now to define the representation brightness for point P which lies in the middle of the surround field. The echo signal Xp corresponding to point P is now at a location in the circuit of the shift registers 5 through 8 which specifically corresponds to a delay of two stored lines (including dead time R) plus $\tau/2$. The signal $x_p$ deriving herefrom thus at the output of the shift register 7 after a delay in a delay register 15 is supplied to the one input of a ratio former 14. The output sum signal S of the sample-and-hold circuit 11 is supplied to the other input of the ratio former 14 after prior dynamic limitation. A root former 13 which forms the root of the sum signal S (corresponding to the double summation as represented in the preceding equation) serves as a dynamic limiter. Hereby, the dynamic range of the signal $x_p$ is halved (as measured in decibels) when the surround field is dark. From a maximum possible eighty decibels close to the skin, thus, forty decibels ensue upon complete compression; this corresponds to an amplitude range which can be well represented precisely as brightness modulation. However, the more the surround field fills up with image points, the smaller the compression becomes, since the denominator signal depends less and less from the intensity of the echo actually to be represented.

In this connection, it can also be desirable to design the degree of compression (division factor of the dynamic range in logarithmic measure) variably. This can occur either in the form of an actuator to be operated externally or automatically. Automation lies at hand if one wishes to adapt the compression to the different signal-to-noise ratio of the image for different depths. In this case, the compression must decrease in relation to depth. Variability of the compression demands the variation of the exponent in the denominator (from the value of $\frac{1}{2}$ given within component 13). This, however, may be best attained by computing (processing the signal) logarithmically. A sample embodiment for this is shown in FIG. 4.

For the ratio formation in the embodiment of FIG. 4, a control amplifier 17 (electrically variable amplification factor) with the exponential control characteristic $$v = v_o e^{-Ky}$$

is now employed.

If the output sum signal S of the sample-and-hold circuit 11 is now first supplied to a logarithmizing element 18 and the control input of the control amplifier 17 thus subsequently loaded with the logarithm of the sum signal, then, with $$y = A \ln S$$

the output signal of the control amplifier 17 ensues at $$X_p = \frac{x_p \cdot v_o}{S^{KA}}.$$

The factor K·A can now be varied as described by means of variation of the amplification factor A at an amplifier 19 between the logarithmizing element 18 and the amplification control input (y) of the control amplifier 17. For the case K·A = $\frac{1}{2}$, root formation and thus a halving of the dynamic range again ensues as in the exemplary embodiment of FIG. 1.

In both cases—i.e., dynamic compression of an alternating signal by means of direct root formation or by means of root formation on the basis of exponent selection according to logarithmization—dynamic limited analog elements, for example, analog delay lines, can be particularly advantageously employed without the threat of information loss. The latter is of interest particularly in electronic sector scan by means of an untrasonic array. Even for the intermediate storage of image parts as it is necessary for the computer-assisted improvement of cross-resolution, the use of analog stores has advantages because a smaller total technical outlay ensues than in complete digital data processing with the high data flows connected therewith.

In the exemplary embodiments of FIGS. 1 through 4, the original echo signal, i.e. which has not yet been compressed in its dynamic range, is offered to the shift registers 5 through 8. Of course, one can also proceed in such manner that the original signal is compressed by means of a suitable signal compressor and the compressed signal is then conducted to the shift registers. This image compressed in advance without consideration of the surround field also continues to contain information concerning bright and dark areas which can be relatively well evaluated. This information, however, can then be exploited as a control criterion in the sense that the amplification is reduced or, respectively, the compression is cancelled everywhere where the image compressed in advance already appears bright. In this case, an ac amplifier should serve as signal compressor whose amplification factor adjusts itself in such manner that the amplitudes of the alternating or high frequency signal are non-linearly influenced according to a pre-selectable characteristic curve. The influencing should ensue specifically for the compression of the dynamic range of the amplitudes according to a root law or logarithmic law. For expansion after the accomplished consideration of the surround field, the inverse non-linear function, specifically thus the quadrature or an exponential law, would come into consideration as functions. Specifically upon the employment of a controlled amplifier, both polarities of the input signal are considered. This makes it possible to either make do with a full-wave rectification on the side of the lower dynamic range with the shortest possible integration time constant for the pulse form or to evaluate separately according to polarity (reflection on a sonically hard or, respectively, sonically soft reflector). However, direct current values must be co-transmitted or, respectively, stored, since in the case of signal compression it is a matter of a controlled non-linearity, which simultaneously generates direct current components anew out of a pure alternating signal. With the help of such non-linear amplifiers, however, it is possible to embed dynamic range limited modules (shift registers, peak value rectifiers, dividers) between a signal compressor and a signal expander from the very outset. In the case of these modules, thus, recourse can be had to component parts which function on an analog basis and can be readily purchased.

Upon compression of the original signal, for example, according to the relationship $$x_K \frac{x}{\sqrt{|x|}}$$

the expansion can ensue for example quadratically according to the relationship $$x_E = \frac{x_p}{\sqrt{|x_p|}} \cdot \frac{|x_p|}{\sqrt{|x_p|}} = x_p$$

Thereby, the expander can lie in front of the actual ratio former. Only the ratio former thus lies outside of the processing area of compressed dynamic range; accordingly, therefore, it receives the decompressed signal of high dynamic range and must therefore, in this type of signal processing, be of particularly high value. The situation, however, is simplified when the sequence of ratio former and expander is inverted; in this case, however, the sum signal for the ratio former must proceed via an additional root former. Only in that manner does one receive the same output signal as before. One achieves a particular simplification, however, upon modification of the sample embodiment of FIG. 4 in the manner just described.

If in this sample embodiment, thus, a signal compressor is connected in advance of the register circuit 5 through 8, then the logarithmizer 18 and the control amplifier 17 can be immediately included in the zone of limited dynamic range. Only after the control amplifier do the expander and rectifier then follow. Upon formation of the sum peak value and the subsequent temporal summing before logarithmization, a signal then ensues at the output of the control amplifier with the relationship.

$$z = \frac{x_p}{\sqrt{|x_p|}} v_0 e^{-KA \ln \sqrt{|\hat{x}|}} = \frac{v_0 \cdot \frac{x_p}{\sqrt{|x_p|}}}{\left(\sqrt{|\hat{x}|}\right)^{K \cdot A}}$$

Upon decompression in the expander according to the ratio $$z \cdot |z|$$

there ensues the decompressed output signal $$x_E = \frac{v_0^2 \cdot \frac{x_p}{\sqrt{|x_p|}} \cdot \frac{|x_p|}{\sqrt{|x_p|}}}{\left(\sqrt{|\hat{x}|}\right)^{2KA}}$$

with the adjustment $$2KA = 1$$

when the decompressed output signal then again proceeds according to the root function $$x_E = v_0^2 \cdot \frac{x_p}{\sqrt{|\hat{x}|}}.$$

Since the dynamic range remains limited after the control amplifier, the sequence of expander and rectifier could be interchanged.

If, however, one now displaces the rectifier by an additional position to the front, which can be carried out without difficulties because of the preceding compression, then the possibility ensues of allowing the signal processing to precede in the logarithmic, so that no independent expander is now required. The function of an exponential depth compensation, too, can be codisposed in the logarithmic processing part, so that no additional depth compensation amplifier is required. An embodiment modified in this manner is shown in FIG. 5.

Figure 5:
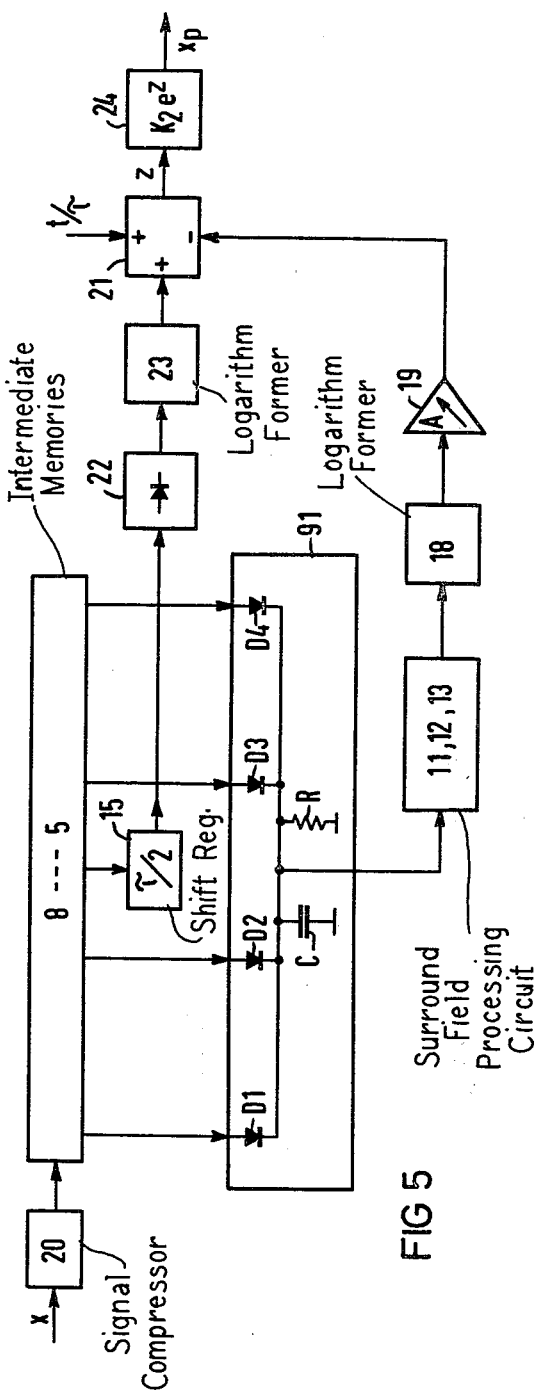
FIG. 5 illustrates a third embodiment with signal compression for the input dynamic range and logarithmic depth compensation for output signals.

In FIG. 5, a signal compressor 20 is connected in advance of the registers 5 through 8. The signal compressor 20 compresses the dynamic range of the incoming signal x in the manner described above according to the function $$x_K = \frac{x}{\sqrt{|x|}}$$

The signal $\sqrt{|\hat{x}|}$ lies at the output of the sum peak value former 91 formed with diodes D1 through D4, capacitances C and resistances R after the temporal summing-up and root formation in the component elements 11 through 13.

This signal is converted in the logarithmizing element 18 to $\ln \sqrt{|\hat{x}|}$. The logarithmized signal is delivered via the amplifier 19 to the subtraction input of a sum-difference former 21. This has two additional summing inputs. The signal $x_p/\sqrt{|x_p|}$ occurring at the output of the delay element 15 is conducted to the first summing input after rectification in a rectifier 22 and logarithmization according to the relationship $K_1 \ln \sqrt{|\hat{x}_p|}$ in a further logarithmizing element 23. A time linear ramp function $t/\tau$ for the necessary depth compensation is delivered to the other summing input. When the signal z which is thus developing at the output of the difference-sum former 21 is formed according to the relationship $K_2 e^z$, then there ensues for the output signal of the exponental forming element 24 the relationship $$x_p = K_2 e^{K_1 \ln \sqrt{|x_p|} - A \ln \sqrt{|\hat{x}|} + \frac{t}{\tau}}$$

$$= K_2 \frac{\left(\sqrt{|x_p|}\right)^{K_1}}{\left(\sqrt{|\hat{x}|}\right)^A} \cdot e^{t/\tau}$$

With $$K_1 = 2; K_2 = 1; A = 1$$

one finally receives the form of the exponential depth compensation to $$x_p = \frac{|x_p|}{\sqrt{|\hat{x}|}} e^{t/\tau}$$

The logarithmization does not, as in the present case, have to be executed in separate blocks at the output of the processing circuit. It can also be executed in the signal compressor at the input side, namely then when the logarithmically functioning signal compressor is simultaneously a depth compensation amplifier or when a time-linear ramp function at the signal compressor takes care of the necessary depth compensation.

In all of the exemplary embodiments of FIGS. 1 through 5, analog storage chain circuits, particularly so-called charge coupled device circuits (CCD-circuits), are preferred as shift registers because a good synchronization with the line frequency is possible with these. However, acoustic delay lines can also be employed as they are usual, for example, in color television devices as PAL-lines.

It will be apparent that many modifications and variations may be effected without departing from the scope of the novel concepts and teachings of the present invention.

I claim as my invention:

1. A method for producing and recording ultrasonic sectional images, said method comprising:
    (a) scanning an examination subject line-by-line with ultrasonic transmission signals and producing from the resulting echo signals ($E_n$ through $E_{n+4}$) representing successive lines of an ultrasonic image of the examination subject, a time series of echo lines ($Z_n$ through $Z_{n+4}$) occurring at a selected echo line rate, (b) writing a selected number of echo lines ($Z_n$ through $Z_{n+3}$) into a corresponding number of intermediate memories (5, 6, 7, 8) of a first memory unit such that echo signal information is available for obtaining a mean value (S) of echo intensity of a pertinent field (U) in the vicinity of a given point (P) of the ultrasonic image, (c) reading out from the intermediate memories (5, 6, 7, 8) samples ($X_{i,n}$) from the respective stored echo lines ($Z_n$ through $Z_{n+3}$), (d) forming from echo signal information comprising the intensities of the samples ($x_{i,n}$) as read out over a given time interval ($\tau$), representing a desired depth for the pertinent field (U) in the vicinity of the given point (P) of the ultrasonic image, a mean value signal (S) representing the mean value of the pertinent field (U) in the vicinity of the given point (P) of the ultrasonic image, (e) supplying a point-representative echo signal (xp) in accordance with the echo intensity for the given point (P) of the ultrasonic image, and (f) forming a relationship signal (e.g. $x_p/\sqrt{S}$) in accordance with a predetermined relationship of the point-representative echo signal (xp) to the mean value signal (S) for the given point, and recording a signal in accordance with such relationship signal to represent the given point (P) of the ultrasonic image, (g) the forming of the mean value signal (S) for the pertinent field (U) in the vicinity of the point (P) according to step (d) being effected by:

(g1) supplying from the echo signal information successive samples ($x_{i,n}$) to a summing means (9) so as to form successive sum signals representing the sums of the intensities of points of the successive echo lines ($Z_n$ through $Z_{n+4}$) defining the pertinent field (U) in the vicinity of the given point (P), and (g2) supplying the successive sum signals from the summing means (9) to a second memory unit (11), and to a third memory unit (12) having a time delay corresponding to said given time interval ($\tau$) to provide as its output successive delayed sum signals, and in the second memory unit (11) summing the successive sum signals supplied thereto, and supplying as the mean value signal (S) for the given point (P) a signal which is a function of the difference between the summation of the sum signals supplied to the second memory unit (11) during said given time interval ($\tau$) and the output from the third memory unit (12).

2. Method according to claim 1, characterized in that echo signal information stored by the intermediate memories (5 through 8) are simultaneously scanned to provide respective samples corresponding to the same depth for each scanning line which are simultaneously relayed to the summing means (9) for summing.

3. Method according to claim 1, characterized in that the echo intensity of the field for each point, is placed in relationship according to step (f) to a point-representative echo signal (xp) which is tapped at the intermediate memories (5 through 8) after a delay time which corresponds to half the number of stored lines for defining the pertinent field, plus half the delay time of the third memory unit (12).

4. Method according to claim 3, with the step (b) being effected in that echo lines are continuously clocked into and through shift registers (5 through 8) as intermediate memories; and with step (c) being effected in that echo signal information resulting at the outputs of each shift register represent the samples which together with echo signal information respectively occurring at the moment at the input of the respectively first shift register are summed in the summing means (9).

5. Method according to claim 4, characterized in that the echo signal information is clocked into the shift registers (5 through 8) and is clocked through said shift registers which are connected in series.

6. Method according to claim 1, characterized in that mean value signals (S) for successive points of the ultrasonic image are subjected to dynamic compression via a root former (13) such that the relationship signal of step (f) is a function of the square root of the respective mean value signal.

7. Method according to claim 1 characterized in that, for the purpose of relationship formation according to step (f), the mean value signal (S) is supplied after logarithmization in a logarithm former (18), as a control signal (y) to the control input for controlling the amplification degree of a control amplifier (17) with an exponential control characteristic with a negative exponent ($v_o \cdot e^{-Ky}$) at whose amplification input is supplied the point-representative echo signal respectively to be imaged.

8. Method according to claim 7, characterized in that the logarithmized mean value signal is supplied via an interposed signal amplifier (19), so that the amplification degree (A) of such signal amplifier (19) determines the denominator value ($S^{KA}$) of the output from the control amplifier (17).

9. Method according to claim 8, the exponent having a value $\frac{1}{2}$ to provide root dependency and, thus, halving of the dynamic range.

10. Method according to claim 1, characterized in that the echo signal information (x) is already compressed for the purpose of dynamic limitation before writing into the intermediate memories (5 through 8).

11. Method according to claim 10, characterized in that the compression ensues according to a root or logarithm function.

12. Method according to claim 10, characterized in that echo signals to be imaged are decompressed by means of an expander before the relationship formation of step (f) or the relationship signal produced by step (f) itself is decompressed.

13. Method according to claim 12, characterized in that the expansion ensues according to quadratic or exponential law.

14. Method according to claim 10, characterized in that the point representative echo signals ($x_p$) respectively to be imaged are logarithmized after rectification in a rectifier (22) by means of a logarithm element (23) and the logarithmized signal is supplied to a first summing input of a sum/difference former (21) whose second summing input is charged with a ramp function ($t/\tau$) and whose subtraction input is charged with the logarithmic sum signal for the relationship formation (FIG. 5).

15. Apparatus for producing and recording ultrasonic sectional images, said apparatus comprising:

(a) scanning means for scanning an examination subject line-by-line with ultrasonic transmission signals and producing from the resulting echo signals ($E_n$ through $E_{n+4}$) representing successive lines of an ultrasonic image of the examination subject, a time series of echo lines ($Z_n$ through $Z_{n+4}$) occurring at a selected echo line rate, (b) a first memory unit comprising a prescribed number of intermediate memories (5 through 8) coupled with said scanning means for storing a corresponding number of echo lines ($Z_n$ through $Z_{n+3}$) such that echo signal information is available for obtaining a mean value (S) of echo intensity of a pertinent field (U) in the vicinity of a given point (P) of the ultrasonic image, with each intermediate memory having a capacity to store one of said echo lines, (c) read out means comprising a clock pulse generator (10) coupled with said intermediate memories (5 through 8) for reading out from the intermediate memories (5, 6, 7, 8) samples ($x_{i,n}$) from the respective stored echo lines ($Z_n$ through $Z_{n+3}$), (d) mean value signal forming means (9 through 12) coupled with said intermediate memories (5 through 8) for forming from echo signal information comprising the intensities of the samples ($x_{i,n}$) as read out from said intermediate memories over a given time interval ($\tau$), representing a desired depth for the pertinent field (U) in the vicinity of the given point (P) of the ultrasonic image, a mean value signal (S) representing the mean value of the pertinent field (U) in the vicinity of the point (P) of the ultrasonic image, (e) supplying means (15) coupled with said first memory unit for supplying a point-representative echo signal (xp) in accordance with the echo intensity for the given point (P) of the ultrasonic image, and (f) relationship forming means coupled with said mean value signal forming means (9 through 12) and with said supplying means (15) for forming a relationship signal (e.g. $x_p/\sqrt{S}$) in accordance with a predetermined relationship in the point-representative echo signal (xp) to the mean value signal (S) for the given point, (g) said mean value signal forming means comprising a summing means (9) coupled with said intermediate memories (5 through 8) so as to form successive sum signals representing the sums of the intensities of points of the successive echo lines ($Z_n$ through $Z_{n+4}$) defining the pertinent field (U) in the vicinity of the given point (P), and (h) said mean value signal forming means further comprising a second memory unit (11) coupled with said summing means (9) for receiving the successive sum signals from said summing means (9), and a third memory unit (12) coupled with said summing means (9) and having a time delay corresponding to said given time interval ($\tau$) to provide as its output successive delayed sum signals;

(i) said second memory unit (11) being a sample-and-hold circuit having a summing input coupled with said summing means (9) for summing the successive sum signals supplied thereto, and having a subtraction input coupled with said third memory unit (12) so as to supply as the mean value signal (S) for the given point (P) a signal which is a function of the difference between the summation of the sum signals supplied to the second memory unit (11) during said given time interval ($\tau$) and the output from the third memory unit (12).

16. Apparatus according to claim 15, with said summing means comprising peak detectors (91) for sensing the peak value among the samples from the intermediate memories (5 through 8).

17. Apparatus according to claim 15, with said first memory unit comprising a series connection of analog shift registers (5 through 8) as intermediate memories which are connected respectively to said summing means (9).

18. Apparatus according to claim 15, with a signal compressor (20) coupled between said scanning means and said intermediate memories (5 through 8) (FIG. 5).

19. Apparatus according to claim 18, with said signal compressor (20) functioning according to root or logarithm law.

20. Apparatus according to claim 18, with an expander for the echo signals coupled in series with said relationship forming means.

21. Apparatus according to claim 20, with said expander functioning according to a quadratic or exponential law.

22. Apparatus according to claim 18, with said supplying means having connected therewith a series circuit for the echo signal to be depicted, comprising a rectifier (22) and a logarithmizing element (23), and said mean value signal forming means comprising a sum-difference former (21) with a first summing input coupled with said series circuit for receiving the rectified and logarithmized echo signal, with a second summing input for receiving a ramp function ($t/\tau$) and with a subtraction input for receiving a logarithmic sum signal, and a logarithmizing circuit (18) interposed between said sample-and-hold circuit (11) and said subtraction input of said sum-difference former (21).

* * * * *